United States Patent [19]

Nelson

[11] Patent Number: 4,812,582

[45] Date of Patent: Mar. 14, 1989

[54] PROCESS FOR PREPARING ALDOL INTERMEDIATES

[75] Inventor: Stephen J. Nelson, County of Kalamazoo, Mich.

[73] Assignee: The Upjohn Company, Kalamazoo, Mich.

[21] Appl. No.: 47,230

[22] Filed: May 6, 1987

Related U.S. Application Data

[62] Division of Ser. No. 757,659, Jul. 22, 1985, Pat. No. 4,680,419.

[51] Int. Cl.$^4$ .................. C07D 317/26; C07C 49/203; C07C 49/17
[52] U.S. Cl. ..................................... 549/214; 549/453; 549/416; 549/415; 549/414; 556/444; 556/443; 556/440; 560/264; 560/262; 560/112; 560/65; 560/64; 560/23; 560/22; 560/20; 560/18; 568/415; 568/414; 568/50; 568/45
[58] Field of Search ............... 549/453, 214, 414, 415, 549/416; 568/415, 414, 50, 45; 560/18, 20, 22, 23, 64, 65, 112, 262, 264; 556/440, 443, 444

[56] References Cited

U.S. PATENT DOCUMENTS

| | | | |
|---|---|---|---|
| 3,950,360 | 4/1976 | Aoki et al. | 260/343.2 R |
| 3,984,564 | 10/1976 | Aoki et al. | 424/174 |
| 3,992,551 | 11/1976 | Aoki et al. | 424/283 |
| 4,093,629 | 6/1978 | Fisher | 260/326.23 |
| 4,144,352 | 3/1979 | Putter | 424/269 |
| 4,408,059 | 10/1983 | Smith et al. | 549/214 |

FOREIGN PATENT DOCUMENTS

82/01658 11/1982 PCT Int'l Appl. .

OTHER PUBLICATIONS

Fisher, M. H. and Mrozik, H., *The Avermectin Family of Macrolide-Like Antibiotics*, pp. 553–606, "Macrolide Antibiotics: Chemistry, Biology, and Practice", ed. S. Moura, Academic Press (1984).
Tetrahedron Lett., No. 10, pp. 711–714 (1975).
Journal of Antibiotics, vol. 29, No. 6, Jun., 1976, pp. 76-35 to 76-42 and pp. 76-14 to 76-16.
Burg, R. W. et al., "Avermectins, New Family of Potent Anthelmintic Agents: Producing Organism and Fermentation", Antimicrobial Agents and Chemotherapy, vol. 15, No. 3, Mar. 1979, pp. 361–367.
Takiguchi, Y. et al., "Milbemycins*, A New Family of Macrolide Antibiotics: Fermentation, Isolation and Physico-Chemical Properties", Journal of Antibiotics, vol. 33, No. 10, Oct., 1980, pp. 1120–1127.
Williams, D. R. et al., "Total Synthesis of Milbemycin $\beta_3$", J. Am. Chem. Soc., 104, pp. 4708–4710 (1982).
Smith, A. B. III et al., "Total Synthesis of Milbemycin $\beta_3$", J. Am. Chem. Soc., 104, pp. 4015–4018 (1982).
Mori, K. et al., "Synthesis of Three Steroisomeric Forms of 2,8-dimethyl-1,7-dioxaspiro[5,5]undecane, The Main Component of the Cephalic Secretion of Andrena Wilkella", Tetrahedron, 37, pp. 3221–3225.
Mori, K. et al., "Synthesis of Three Steroisomeric Forms of 2,8-dimethyl-1,7-dioxaspiro[5,5]undecane, The Main Component of the Cephalic Secretion of Andrena Wilkella", Heterocycles, vol. 15, 1981, pp. 1171–1174.
Nakahara Y. et al., "Synthetic Studies of Antibiotic A23187 I. Chiral Synthons for C9–C13 and C14–C20", Tetrahedron Lett., 1981, pp. 3197–3200.
Evans, D. A. et al., "Studies Directed Towards the Total Synthesis of the Ionophore Antibiotic A-23187", Tetrahedron Lett., 1978, pp. 727–730.
Cresp, T. M. et al., "An Approach to the Synthesis of Ionphores Related to A23187", Tetrahedron Lett., 1978, pp. 3955–3958.
Baker, R. et al., "The Chemistry of Spiroketals, Enantiospecific Synthesis of the Spiroketal Units of Avermectins $B_{1b}$ and $B_{2B}$", J. Chem. Soc., Chem. Commun., pp. 309–311 (1985).
Hanessian et al., "Stereocontrolled Synthesis of the Spiroketal Unit of Avermectin $B_{1a}$ Agylone", J. Org. Chem., vol. 48, pp. 4427–4430 (1983).
Godoy, J. et al., "Synthesis of the Spiroketal Unit Related to the Avermectins and Milbemycins", J. Chem. Soc., Chem. Commun., pp. 1381–1382 (1984).
Kocienski, P. et al., "A Synthesis of the Spiroketal Moiety of Milbemycin $\beta_3$", J. Chem. Soc., Chem. Commun., pp. 571–573 (1984).
Williams, D. R. et al., "Synthetic Studies of 1,7-dioxaspiro[5,5]undecan-4-ones", Tetrahedron Lett., vol. 24, No. 5, pp. 427–430 (1983).
Kocienski, P. et al., "A New Synthesis of 1,7-dioxaspiro[5,5]undecanes. Applications to a Rectal Gland Secretion of the Olive Fruit Fly (*Dacus oleae*)", Tetrahedron Lett., vol. 24, No. 36, pp. 3905–3906 (1983).
Kay, I. T. et al., "Spiroketals: The Synthesis of an Olive Fly Pheromone Component, 4-hydroxy-1,7-Dioxaspiro[5,5]undecane, via a Novel Cation-Olefin Cyclisation Step", Tetrahedron Lett., vol. 24, No. 52, pp. 5915–5918 (1983).
Kocienski, P. et al., "A Synthesis of Talaromycin$\beta$", J. Chem. Soc., Chem. Commun., pp. 151–152 (1984).
Heathcock, C. H. et al., "Acyclic Stereoselection-13. Aryl Esters: Reagents for Threo-Aldolization", Tetrahedron, 37, pp. 4087–4095 (1981).
Heathcock, C. H. et al., "Acyclic Stereoselection. 11. Double Stereodifferentiation as a Method for Achieving Superior Cram's Rule Selectivity in Aldol Condensations with Chiral Aldehydes", J. Org. Chem., 46, pp. 1296–1308 (1981).
Corey, E. J. et al., "Stereospecific Total Synthesis of Prostaglandins $E_3$ and $F_{3a}$", J. Amer. Chem. Soc., 93, pp. 1490–1493 (1971).
Fieser, L. F. et al., *Reagents for Organic Synthesis*, John Wiley & Sons, N.Y., N.Y., pp. 656–659 (1967).

*Primary Examiner*—Nicky Chan
*Attorney, Agent, or Firm*—William G. Jameson

[57] ABSTRACT

This invention pertains to a new method for killing and controlling worms (Helminths), new formulations for killing and controlling worms in animals, new chemical compounds, and a new synthesis of northern hemisphere intermediates for the synthesis of milbemycin and avermectin macrolides.

3 Claims, No Drawings

PROCESS FOR PREPARING ALDOL INTERMEDIATES

This application is a division of application Ser. No. 757,659 filed July 22, 1985, now U.S. Pat. No. 4,680,419.

SUMMARY OF THE INVENTION

This invention pertains to a new method for killing and controlling worms (Helminths), new formulations for killing and controlling worms in animals, new chemical compounds, and a new synthesis of northern hemisphere intermediates for the synthesis of milbemycin and avermectin macrolides.

The anthelmintic spiroketals have the general structural formula XIX.

BACKGROUND OF THE INVENTION

The milbemycins and avermectins are a series of macrolide antibiotics known to have closely related chemical structures and to exhibit highly potent anthelmintic, insecticidal, ectoparasiticidal and acaricidal activity. See M. H. Fisher and H. Mrozik, The Avermectin Family of Macrolide-Like Antibiotics, pp. 553–606, Macrolide Antibiotics: Chemistry, Biology, and Practice., ed. S. Omura, Academic Press (1984).

The known preparative procedures for these microlides have employed fermentation techniques or lengthy synthesis unsuitable for preparation of various analogs.

The fermentation and isolation procedures, and the chemical structures and properties of the milbemycins and avermectins, are more fully described in U.S. Pat. Nos. 3,950,360; 3,984,564; 3,992,551; 4,093,629; and 4,144,352; Tetrahedron Letters, No. 10, pages 711–714, 1975; Journal of Antibiotics, Vol. 29, No. 6, June, 1976, pages 76-35 to 76-42 and pages 76-14 to 76-16; Antimicrobial Agents and Chemotherapy, Volume 15, No. 3, March 1979, pages 361–367; and Journal of Antibiotics, Volume 33, No. 10, October, 1980, pages 1120–1127.

The total synthesis of milbemycin $\beta_3$ is described in D. R. Williams et al., J. Am. Chem. Soc., 104, 4708–4710 (1982) and A. B. Smith et al., J. Am. Chem. Soc., 104, 4015–4018 (1982).

A lengthy synthesis of milbemycin $\beta_3$ is also described in International Patent Application Number: PCT/US/82/01658, filed Nov. 22, 1982 and U.S. Pat. No. 4,408,059. At column 7, lines 42–51 of U.S. Pat. No. 4,408,059 the applicants speculate that a number of compounds, particularly the spiroketal compounds of Formula XXIV, include the chemical structure responsible for the biological activity of the various milbemycin and avermectin macrolides, and hence may themselves have utility as anthelmintic, insecticidal, ectoparasiticidal or acaricidal agents significantly simplified in chemical structure in comparison with the prior art compounds exhibiting similar biological activity.

The literature contains a number of syntheses of the 1,7-dioxaspiro[5.5]undecane system, many of which depend the construction of a 1,9-dihydroxy-5-oxononane followed by inramolecular ketalization to generate the spiroketal. See, for example, K. Mori and K. Tanida, Synthesis of Three Stereoisomeric Forms of 2,8-Dimethyl-1,7-dioxaspiro[5.5]undecane, The Main Component of the Cephalic Secretion of Andrena Wilkella, Tetrahedron, 1981,37,3221; K. Mori and K. Tanida, Synthesis of Three Stereoisomeric Forms of 2,8-Dimethyl-1,7-dioxaspiro[5.5]undecane, The Main Component of the Cephalic Secretion of Andrena Wilkella, Heterocycles, 1981,15,1171; Y. Nakahara et al, Synthetic Studies of Antibiotic A23187 I. Chiral Synthons for C9-C13 and C14-C20, Tetrahedron Lett., 1981,3197; D. A. Evans et al, Studies Directed Towards the Total Synthesis of the Ionophore Antibiotic A-23187, Tetrahedron Lett., 1978,727; T. M. Cresp et al, An Approach to The Synthesis of Ionphores Related to A23187, Tetrahedron Lett., 1978,3955. Other less general methods for preparing 5.5-spiroketals have been reported. See, for example, R. Baker et al, The Chemistry of Spiroketals.Enantispecific Synthesis of the Spiroketal Units of Avermectins $B_{1b}$ and $B_{2b}$, J. Chem. Soc., Chem. Commun., 309–11, 1985; Hanessian, et al., Stereocontrolled Synthesis of the Spiroketal Unit of Avermectin $B_{1a}$ Agylone, J. Org. Chem., 1983, 48, pp 4427-30; J. Godoy et al., Synthesis of the Spiroacetal Unit Related to the Avermectins and Milbemycins, J. Chem. Soc., Chem. Commun., 1381–82, (1984); P. Kocienski et al., A Synthesis of the Spiroacetal Moiety of Milbemycin $\beta_3$, J. Chem. Soc., Chem. Commun., 571–73, (1984); D. R. Williams et al., Synthetic Studies of 1,7-dioxaspiro[5.-5]undecan-4-ones, Tetrahedron Letters, Vol. 24, No. 5, p 427–30, 1983; P. Kocienski et al., A New Synthesis of 1,7-dioxaspiro[5,5]undecanes. Application to a Rectal Gland Secretion of the Olive Fruit Fly (Dacus oleae), Tetrahedron Letters, Vol. 24, No. 36, p 3905–06, 1983; I. T. Key et al., Spiroketals: The Synthesis of an Olive Fly Pheromone Component, 4-hydroxy-1,7-Dioxaspiro[5.5]undecane, via a Novel Cation-Olefin Cyclisation Step, Tetrahedron Letters, Vol. 24, No. 52, p 5915–18, 1983; P. Kocienski et al., A synthesis of Talaromycin B, J. Chem. Soc., Chem. Commun., 151–52, 1984.

K. J. Bruza, Studies of Synthetic Methodology Utilizing Cyclic Vinyl Ethers, Ph. D. Thesis, U of Michigan, 1979, describes the preparation of 6-oxo-2-methyldecane-1,2,10-triol which cyclizes to a 2,7-dioxabicyclo[3.2.1]octane in contrast to the dioxa[5.5]spiroketal system of the subject invention.

The diseases or groups of diseases described generally as helminthiasis are due to infection of the animal with parasitic worms known as helminths. Helminthiasis and helminthosis are prevalent and may lead to serious economic problems in sheep, swine, cattle, goats, dogs, cats, horses, poultry and man. Among the helminths, the groups of worms known as nematodes, trematodes and cestodes cause widespread and oftentimes serious infections in various species of animals including man. The most common genera of nematodes and cestodes infecting the animals referred to above are Dictyocaulus, Haemonchus, Trichostrongylus, Ostertagia, Nematodirus, Cooperia, Bunostomum, Oesophagostomum, Chabertia, Strongyloides, Trichuris, Fasciola, Dicrocoelium, Enterobius, Ascaris, Toxascaris, Toxocara, Ascaridia, Capillaria, Heterakis, Ancylostoma, Uncinaria, Onchocerca, Taenia, Moniezia, Dipylidium, Metastrongylus, Macracanthorhynchus, Hyostrongylus, and Strongylus. Some of these genera attack primarily the intestinal tract while others, inhibit the stomach, lungs, liver and subcutaneous tissues. The parasitic infections causing helminthiasis and helminthosis lead to anemia, malnutrition, weakness, weight loss, unthriftiness, severe damage to the gastrointestinal tract wall and, if left to run their course, may result in death of the infected animals.

DETAILED DESCRIPTION OF THE INVENTION

The anthelmintic spiroketals of this invention are represented by Formula XIX wherein A is —CH, —CH$_2$ or —CHOP′;

wherein P′ is C$_1$–C$_5$ alkyl; benzoyl optionally substituted with one, 2 or 3 C$_1$–C$_4$ alkyl, C$_1$–C$_3$ alkoxy, halo, C$_1$–C$_3$ alkylthio, trifluoromethyl, nitro; phenyl(C$_1$–C$_3$)alkyl optionally substituted with one, 2 or 3 C$_1$–C$_4$ alkyl, C$_1$–C$_4$ alkoxy, halo, nitro or trifluoromethyl; C$_2$–C$_6$ alkoxyalkyl; C$_2$–C$_6$ alkylthioalkyl; C$_1$–C$_6$ alkanoyl; tetrahydropyranyl; C$_1$–C$_4$ alkyl diphenyl silyl; di(C$_1$–C$_4$ alkyl)phenyl silyl; or tri(C$_1$–C$_4$)alkyl silyl;

wherein ==== is a single bond when A is —CH$_2$ or —CHOP′ and a double bond when A is —CH;

wherein B is —CR$_7$R$_8$OR$_9$ or —R$_7$CO;

wherein R$_1$, R$_2$, R$_4$, R$_6$, R$_8$, being the same or different, are hydrogen or C$_1$–C$_5$ alkyl;

wherein R$_7$ is hydrogen, C$_1$–C$_5$ alkyl or C$_2$–c$_6$ alkenyl;

wherein R$_3$ and R$_9$, being the same or different, are hydrogen; C$_1$–C$_5$ alkyl; benzoyl optionally substituted with one, 2 or 3 C$_1$–C$_4$ alkyl, C$_1$–C$_3$ alkoxy, halo, C$_1$–C$_3$ alkylthio, trifluoromethyl, nitro; phenyl(C$_1$–C$_3$)alkyl optionally substituted with one, 2 or 3 C$_1$–C$_4$ alkyl, C$_1$–C$_4$ alkoxy, halo, nitro or trifluoromethyl; C$_2$–C$_6$ alkoxyalkyl; C$_2$–C$_6$ alkylthioalkyl; C$_1$–C$_6$ alkanoyl; tetrahydropyranyl; C$_1$–C$_4$ alkyl diphenyl silyl; di(C$_1$–C$_4$ alkyl) phenyl silyl; or tri(C$_1$–C$_4$)alkyl silyl;

wherein R$_5$ is hydrogen; C$_1$–C$_5$ alkyl; benzoyl optionally substituted with one, 2 or 3 C$_1$–C$_4$ alkyl, C$_1$–C$_3$ alkoxy, halo, C$_1$–C$_3$ alkylthio, trifluoromethyl, nitro; phenyl(C$_1$–C$_3$)alkyl optionally substituted with one, 2 or 3 C$_1$–C$_4$ alkyl, C$_1$–C$_4$ alkoxy, halo, nitro or trifluoromethyl; C$_2$–C$_6$ alkoxyalkyl; C$_1$–C$_6$ alkanoyl; tetrahydropyranyl; C$_1$–C$_4$ alkyl diphenyl silyl; di(C$_1$–C$_4$ alkyl)phenyl silyl; or tri(C$_1$–C$_4$)alkyl silyl; or a mono- or disaccharide.

The synthesis procedure of the present invention is summarized in Schemes A and B. In the various formulas set forth in reaction schemes A and B, the terms are as defined above, Ar is phenyl substituted at the 2-, 2,6- or 2,4,6-positions with C$_1$–C$_5$ alkyl, E is C$_1$–C$_5$alkyl, M is a metal cation such as an alkali earth metal (for example lithium, sodium or potassium), X is chlorine or bromine, and P″, being the same or different, are C$_1$–C$_5$ alkyl, benzoyl optionally substituted with one, 2 or 3 C$_1$–C$_4$ alkyl, C$_1$–C$_3$ alkoxy, halo, C$_1$–C$_3$ alkylthio, trifluoromethyl, nitro; phenyl(C$_1$–C$_3$)alkyl optionally substituted with one, 2 or 3 C$_1$–C$_4$ alkyl, C$_1$–C$_4$ alkoxy, halo, nitro or trifluoromethyl; C$_2$–C$_6$ alkoxyalkyl; C$_2$–C$_6$ alkylthioalkyl; C$_1$–C$_6$ alkanoyl; tetrahydropranyl; C$_1$–C$_4$ alkyl diphenyl silyl; di(C$_1$–C$_4$ alkyl) phenyl silyl; or tri(C$_1$–C$_4$)alkyl silyl; or optionally taken together to form a 1,3-dioxolane ring optionally substituted with one or two C$_1$–C$_5$ alkyl.

The present invention also encompasses novel compounds obtained as, or readily derivable from, the various intermediates prepared during the course of reaction scheme A and B. Such novel compounds include the spiroketal compounds of Formula XIX and XVII, and the aldol products of Formula III and III′, as well as the compounds of formula V, VI, VII, X, XI, XII, XIV, XV, XVI, and XVII.

Certain intermediates of this invention, in particular compounds of Formula IV, VIII and XVII are useful for the preparation of milbemycin and avermectin macrolides and analogs thereof. See, for example, U.S. Pat. No. 4,408,059, J. Am. Chem. Soc., 104, 4708–10 (1982) and J. Am. Chem. Soc., 104, 4015–4018 (1982).

The present invention is described in further detail with reference to reaction scheme A:

Step 1. The kinetic enolate of ketone II is generated by addition of II to a solution of a suitable strong base such as lithium diisopropylamide or potassium hexamethyldisilazide. The gegenion of the enolate may be exchanged for certain other metal cations such as zinc, magnesium, titanium, tin, and the like by addition of the corresponding metal halide. The enolate is generated in a suitably inert solvent such as ether, tetrahydrofuran, hexane, toluene, and the like at temperatures from −100° C. to −15° C., preferably −80° C. to −40° C. Subsequent addition of the aldehyde I at the same temperatures provides the aldol product III.

Step 2. Treatment of the aldol product III with aqueous acid in a suitable organic solvent results in hydrolysis of the protecting group P and the acetonide. Spontaneous intramolecular ketalization yields the spiroketal derivatives IV. Suitable acid catalysts include hydrogen chloride, hydrogen bromide, methane sulfonic acid, sulfuric acid, fluoboric acid, and the like. Preferred is fluoboric acid. Suitable organic solvents include toluene, tetrahydrofuran, ether, glyme, lower alcohols, and the like. Water concentration may be from 0.1 to 20%, preferably 0.5 to 10% based on volume. Acid concentrations may be from 0.05N to 3.0N, preferably 0.1N to 1N, based on total solution volume.

Step 3. The sulfonate ester V is prepared by reaction of IV with a sulfonyl chloride, for example p-toluenesulfonyl chloride, in pyridine at −30° C. to +30° C., preferably −15° C. to +10° C.

Step 4. The nitrile VI is obtained from the sulfonate ester V by reaction with an alkali metal cyanide salt, e.g potassium or sodium cyanide. The reaction is conducted in a suitable solvent such as acetone, acetonitrile, dimethylformamide or dimethylsulfoxide at 0° to 100°; preferably 25° C. to 90° C.

Step 5. Reaction of VI with R$_3$X (when R$_3$ is other than hydrogen) is achieved in a suitable inert solvent, e.g. tetrahydrofuran, toluene, ether, methylene chloride and the like. The reaction is preferably conducted in the presence of an acid acceptor. Suitable acid acceptors include trialkylamines, pyridines, dimethylaminopyridine, imidazole, and the like. Reaction can be conducted at −20° to +50°, preferably −10° to +25°.

Step 6. Reduction of the nitrile of VII is conducted with a dialkylaluminum hydride, such as diisobutylaluminum hydride, in a suitable inert solvent such as THF, ether, toluene, methylene chloride or hexane, at −20° C. to 50° C., preferably 10° C. to 30° C. Hydrolysis of the resultant unisolated imine is achieved by mineral acid, e.g. dilute sulfuric acid workup.

Step 7. Condensation of the aldehyde derived in Step VI with triphenylphosphoranylidene esters IX, where E=lower alkyl of 1–5C, in a suitable solvent provides the E-α,β unsaturated ester X. Suitable solvents include methylene chloride, THF, toluene, acetonitrile, ethyl acetate and hexane. Reaction temperatures may be from 0° to 100°, preferably 20° to 80°.

Step 8. Reduction of the ester X to the alcohol XI is achieved with hydride reducing agents such as lithium aluminum hydride, diisobutylaluminum hydride, lithium borohydride or borane in suitably inert solvents such as ether, methylene chloride, THF or toluene, at temperatures from −80° to +50°, preferably −78° C. to −20° C.

Step 9. Oxidation of the primary alcohol XI derived in Step 8 is achieved with known oxidation reagents including pyridinium chlorochromate, pyridinium dichromate, oxalyl chloride/dimethyl sulfoxide and N-chlorosuccinimide/dimethyl sulfoxide, in an appropriate solvent. Preferred is pyridinium chlorochromate in methylene chloride at temperatures from 0° to 40°, preferably 20° to 40°.

Step 10. Condensation of the aldehyde XII with the hindered aryl esters XIII is achieved under condition similar to Step 1 utilizing the known procedure given by C. H. Heathcock, M. C. Pirrang, S. H. Montgomery and J. Lampe, Tetrahedron, 37, 4087, 1981. The products of this condensation when Ar=2,6-dimethylphenyl are shown by nmr to be exclusively threo or anti adducts as defined by C. H. Heathcock, C. T. White, J. J. Morrison and D. VonDerveer, J. Org. Chem., 46, 1296 (1981).

Step 11. Reaction of the Aldol XIV with $R_5X$ is achieved similarly to that of Step 5.

Step 12. Reduction of the ester products of Step 11 is achieved similarly to Step 8.

Step 13. Oxidation of the alcohol products of Step 12 is achieved similarly to Step 9.

Step 14. Reaction of the aldehyde XVII with organometallic reagents, for example Grignard reagents, is conducted in suitable solvents such as ether or tetrahydrofuran at temperatures from −80° to +30°, preferably at −20° to +10° C. When $R_7$ is hydrogen, M' is a suitable reducing agent such as sodium borohydride, lithium aluminum hydride and diborane. When $R_7$ is $C_1$–$C_5$ alkyl, M' is magnesium or lithium.

Step 15. Reaction of the alcohol XVIII with $R_8X$ is conducted similarly to Step 5.

The aldehyde I utilized in Step 1 is known: E. J. Corey, H. Shirahama, H. Yamamoto, S. Terashima, A. Venkateswarlu and T. K. Schaaf, J. Amer. Chem. Soc., 93, 1490 (1971).

In Compounds II, II', III and III', P, P', and P" represent a protecting group which is stable to the alkaline reaction conditions of Step 1 but is readily hydrolysed under the acidic conditions of Step 2. Suitable protecting groups include silyl derivatives (preferably silyl ethers, for example t-butyldimethyl, triisopropyl, t-butyldipheny silyl ethers), 2-tetrahydropyranyl ethers, alkoxymethyl ethers (for example, methoxymethy and 2-methoxyethoxymethyl), alkoxythiomethyl ethers (for example, methylthiomethylether), benzylethers (for example, benzyl, 4-methoxybenzyl and 2,4-dimethoxybenzyl) and the like. The derivatives are readily prepared from the corresponding 1-hydroxy-5-hexanones according to standard procedures.

The 1-hydroxy-5-hexanones are obtained by procedures reported in the literature, for example, D. R. Williams and B. A. Barner, Tet. Lett., 24, 427 (1983) and N. Lipp, Chem. Ber. 18, 3275 (1885).

Alternatively, the hydroxyhexanones may be obtained by mercuric salt catalysed hydrolysis of the corresponding 1-hydroxy-5-hexynes as described in L. F. Fieser and M. Fieser, Reagents for Organic Synthesis, John Wiley % Sons, N.Y., N.Y., 1967, pp 656–9.

Other oxygen protective groups are set forth in T. W. Greene, Protecting Groups in Organic Synthesis, Wiley, New York, (1981); J. F. W. McOmie, ed. Protective Groups in Organic Chemistry, Plenum Press (1973); and J. Fuhrop and G. Penzlin, Organic Synthesis, Verlang Chemie (1983).

—C— means the carbon content of various hydrocarbon-containing moieties is indicated by a prefix designating the minimum and maximum number of carbon atoms in the moiety. Thus ($C_1$-$C_3$) alkyl refers to alkyl of one to 3 carbon atoms, inclusive or methyl, ethyl, propyl, and isopropyl.

Halogen atom (halo) refers to a bromo, chloro, iodo or fluoro atom.

Examples of $C_1$-$C_4$ alkyl are methyl, ethyl, propyl, butyl and isomeric forms thereof. Examples of $C_1$-$C_3$ alkoxy are methoxy, ethoxy, propyloxy and isomeric forms thereof. Examples of phenyl($C_1$-$C_3$)alkyl substituted with one, 2 or 3 $C_1$-$C_4$ alkyl, $C_1$-$C_4$ alkoxy, halo or trifluoromethyl include 4-chlorobenzyl, 2-methylbenzyl, 4-methoxybenzyl, 2,4-dimethoxybenzyl or 3,4-dimethoxybenzyl. Examples of $C_1$-$C_3$ alkylthio include methylthio, ethylthio and n-propylthio.

Examples of $C_2$-$C_6$ alkoxyalkyl include mono- or dialkoxymethyl, for example methoxymethyl and 2-methoxyethoxymethyl. Examples of $C_2$-$C_6$ alkylthioalkyl, include mono- or dialkylthiomethyl, for example methylthiomethyl and methoxymethylthiomethyl.

Examples of monosaccharrides include oleandrose, glucose, mannose and the like. Examples of disaccharides include sucrose, maltose, and lower (2-3) oligmers of oleandrose.

Preferred A is $CH_2$.

Preferred $R_1$, $R_2$, $R_4$ and $R_6$, being the same or different, are hydrogen or methyl.

Preferred B is —$CH_2OH$ or CHO.

The following detailed examples of the invention are to be construed are merely illustrative, and not limitations of the proceeding disclosure in any way whatsoever. Those skilled in the art will promptly recognize appropriate variations from the procedures both as to reactants as well as to reaction conditions and techniques.

EXAMPLE 1

Preparation of 6-t-butyldimethylsilyloxyhexan-2-one

A solution of methyl lithium-lithium bromide complex in ether is added dropwise to a solution of δ-valerolactone (17.2 g, 0.72 mol) in tetrahydrofuran (200 ml) cooled in a dry ice-acetone bath. After the addition, the solution is stirred at −78° for two hours. Water (5 ml) is added and the mixture allowed to warm to 0°. The mixture is diluted with water (300 ml) and extracted with ether (4×400 ml). The combined extracts are dried over sodium sulfate and concentrated under reduced pressure to leave an oil (14.95 g). A portion of this crude mixture (7.4 g) is dissolved in DMF (30 ml), imidazole (4.3 g, 64 mmol) and t-butyldimethylsilyl chloride (9.6 g, 64 mmol) are added and the mixture stirred at room temperature overnight. The mixture is diluted with water (100 ml) and extracted with hexane (2×250 ml). The extracts are dried over sodium sulfate and concentrated under reduced pressure to leave an oil (14.92 g). Medium pressure chromatography of this mixture (10% ethyl acetate/hexane) on silica gel yields the title compound (9.65 g, 49% based on valerolactone) as an oil.

Anal.: Calc'd for $C_{12}H_{26}O_2Si$: C, 62.55; H, 11.37. Found: C, 61.63; H, 11.38.

PMR (CDCl$_3$): 0.07, 0.93, 1.61, 2.17, 2.49, 3.65 ppm.

EXAMPLE 2

Preparation of 8-t-butyldimethylsilyloxy-1-(2,2-dimethyl-1,3-dioxolan-4-yl)-2-hydroxyoctan-4-one A solution of n-butyl lithium in hexane (119 ml, 1.6M, 0.19 mol) is added dropwise to a solution of diisopropylamine (19.3 g, 0.191 mol) in THF (100 ml) cooled in an ice bath. After the addition, the mixture is stirred for 20 minutes then cooled to −78°. A solution of 6-t-butyldimethylsilyloxy-hexan-2-one (40.0 g, 0.174 mol) in THF is added dropwise. The resultant mixture is stirred for 90 minutes then a solution of 2,2-dimethyl-1,3-dioxolane-4-acetaldehyde (25.1 g, 0.174 mol) in THF (100 ml) is added dropwise. After the addition, the mixture is stirred for 2 hours, then water (10 ml) slowly added. The mixture is warmed to 0°, diluted with water (300 ml) and extracted with ether (2×500 ml). The extracts are washed with saturated brine, dried over sodium sulfate and concentrated under reduced pressure to leave the crude product (63.5 g) an oil. A portion of this material (46 g) is chromatographed on silica gel (2.5 Kg) eluting with 25% ethyl acetate/hexane to give the title compound, 8-t-butyldimethylsiloxy-1-(2,2-dimethyl-1,3-doxolan-4-yl)-2-hydroxyoctan-4-one; (23 g, 49%) an oil.

Anal.: Calc'd for $C_{19}H_{38}O_5Si$: C, 60,92; H, 10.23. Found: C, 61.50; H, 10.49.

PMR ($CDCl_3$): 0.11, 0.95, 1.41, 1.46, 2.57, 3.57, 4.24 ppm.

EXAMPLE 3

Preparation of 4-R,S-hydroxy-2-S,R-hydroxymethyl-6-R,S-1,7-dioxaspiro[5.5]undecane Fluoboric acid (5 ml, 50%) is added at room temperature to a solution of 8-t-butyldimethylsilyloxy-1-(2,2-dimethyl-1,3-dioxolan-4-yl)-2-hydroxyoctan-4-one (25.0 g, 66.7 mmol) in ether (150 ml). The mixture is stirred at room temperature for 30 minutes during which time a precipitate forms. The precipitate is filtered to give the title compound (6.05 g, 44.8%) as a solid, m.p. 121°-2°. Tlc of this material (90% ethyl acetate/hexane) showed only trace of impurities. Two additional crops of the title compound (0.48 g and 0.42 g) are obtained by concentration and trituration with ether/pentane. Other stereoisomers are obtained and can be isolated by silica gel chromatography. An analytical sample of the title compound is recrystallized from acetonitrile, mp 156°-8°.

Anal.: Calc'd for $C_{10}H_{18}O_8$: C, 59.37, H, 8.97 Found: C, 59.21; H, 9,15.

PMR ($CDCl_3$): 1.54, 3.48, 3.86 ppm.

The mass spectra shows m/e 202 (M+).

EXAMPLE 4

Preparation of 4-hydroxy-2-[[(4-methylphenylsulfonyl)oxy]methyl]-1,7-dioxaspiro[5.5]undecane To a stirred suspension of the spiroketal diol, 4-R,S-hydroxy-2-S,R-hydroxymethyl-6-R,S-1,7-dioxaspiro[5.5]undecane, (35.00 g; 173 mmoles) in dry pyridine (175 ml) at −15° under a nitrogen atmosphere is added solid tosyl chloride (34.64 g; 182 mmoles) in a single portion. The reaction mixture is stirred at −10° to −15° for 60 minutes, allowed to warm to room temperature then stirred for another 60 minutes. The reaction mixture is poured into ice water (250 ml) and extracted with ether (2×250 ml). The organic phases are combined, washed with 2N HCl (3×100 ml), saturated sodium bicarbonate, then dried over anhydrous magnesium sulfate. Concentration in vacuo yields the title compound, 4-hydroxy-2-[[(4-methylphenylsulfonyl)oxy]methyl]-1,7-dioxaspiro[5.5]undecane: (45.4 g: 73.6%) as an oil.

PMR ($CDCl_3$): 1.55, 2.47, 3.46, 4.01, 7.34, 7.77 ppm.

EXAMPLE 5

Preparation of 4-hydroxy-1,7-dioxaspiro[5.5]undecaneacetonitrile

A mixture of the tosylate, 4-hydroxy-2-[[(4-methylphenylsulfonyl)oxy]methyl]-1,7-dioxaspiro[5.5]undecane, (87.9 g; 247 mmoles), potassium cyanide (19.3 g; 296 mmoles) and dimethylsulfoxide (300 ml) is heated at 80°-90° for 150 minutes with stirring under a nitrogen atmosphere. After cooling to 25°, the reaction mixture is diluted with ether (1500 ml) and mixed thoroughly. The supernatant is decanted and the extraction process repeated. The combined decantates are washed with saturated sodium chloride and dried over anhydrous magnesium sulfate. Concentration in vacuo gives an oil which is chromatographed (30% ethyl acetate/hexane) to afford the title compound, 4-hydroxy-1,7-dioxaspiro[5.5]undecaneacetonitrile; (28.4 g; 54.7%) as an oil.

PMR ($CDCl_3$): 1.70, 2.47, 3.55, 3.93 ppm.

EXAMPLE 6

Preparation of 4-[(1,1-dimethylethyl)dimethylsilyl]oxy-1,7-dioxaspiro[5.5]undecaneacetonitrile To a mixture of imidazole (9.15 g; 134 mmoles) and 4-hydroxy-1,7-dioxaspiro[5.5]undecaneacetonitrile, (28.4 g; 134 mmoles) in DMF (135 ml) at 0° us added tert-butyldimethylchlorosilane (20.3 g; 134 mmoles). The cooling bath is removed, and the reaction mixture allowed to stir at ambient temperature for 6 hours. The reaction mixture is poured into water (900 ml) and extracted with hexane (2×300 ml). The extracts are combined, dried over anhydrous sodium sulfate and concentrated in vacuo to afford the title compound, 4-[(1,1-dimethylethyl)dimethylsilyl]oxy-1,7-dioxaspiro[5.5]undecaneacetonitrile; (39.2 g; 89.5%) as an oil. Chromatography (10% ethyl acetate/hexane) provided an analytical sample.

Anal.: Calc'd for: $C_{17}H_{31}NO_3Si$: 62.73; H, 9.60; N, 4.30. Found: C, 62.41; H, 9.63; N, 4.03.

PMR ($CDCl_3$): 0.19, 0.99, 1.69, 2.60, 3.65, 4.07 ppm.

EXAMPLE 7

Preparation of 4-[(1,1-dimethylethyl)dimethylsilyl]oxy-1,7-dioxaspiro[5.5]undecaneacetaldehyde To a solution of 4-[(1,1-dimethylethyl)dimethylsilyl]oxy-1,7-dioxaspiro[5.5]undecaneacetonitrile, (37.0 g; 114 mmoles) in methylene chloride (400 ml) at 25° is added dropwise a solution of 1M DIBAL in methylene chloride (114 ml; 114 mmoles). The reaction is moderately exothermic. After ninety minutes methanol (15 ml) is cautiously added dropwise (foaming). After ten minutes the reaction mixture is poured into a mixture of 6.67N sulfuric acid (200 ml) and crushed ice (400 g). The mixture is intermittently shaken over a period of ten minutes. The organic phase is separated, washed with saturated sodium chloride, dried over anhydrous magnesium sulfate, and concentrated in vacuo to afford the title compound, 4-[(1,1-dimethylethyl)dimethylsilyl]oxy-1,7-dioxaspiro[5.5]undecaneacetaldehyde; (34.2 g; 91.7%) as an oil.

PMR (CDCl$_3$): 0.15, 0.97, 1.64, 2.61, 3.64, 4.18, 9.91 ppm.

EXAMPLE 8

Preparation of ethyl 4-[[4-(1,1-dimethylethyl)silyl]oxy-1,7-dioxaspiro[5.5]undec-2-yl]-2-methyl-2E-butenoate A mixture of (carbethoxyethylidene)triphenylphosphorane (41.3 g; 114 mmoles) and 4-[(1,1-dimethylethyl)dimethylsilyl]oxy-1,7-dioxaspiro[5.5]undecaneacetaldehyde, (34.2 g; 104 mmoles) in acetonitrile (400 ml) is refluxed under an atmosphere of nitrogen with stirring for two hours. The mixture is concentrated in vacuo and the residue chromatographed (10% ethyl acetate/hexane) to give the title compound, ethyl 4-[[4-(1,1-dimethylethyl)silyl]oxy-1,7-dioxaspiro[5.5]undec-2-yl]-2-methyl-2E-butenoate; (32.1 g; 68.3%) as a clear, yellow oil.

Anal.: Calc'd for: C$_{22}$H$_{40}$O$_5$Si: C, 6404; H, 9.77 Found: C, 64.46; H, 10,26.

PMR (CDCl$_3$): 0.15, 0.96, 1.36, 1.66, 1.95, 2.45, 3.61, 3.91, 4.26, 6.97 ppm.

EXAMPLE 9

Preparation of 4[[4-(1,1-dimethylethyl)silyl]oxy-1,7-dioxaspiro[5.5]undec-2-yl]-2-methyl-2E-butenol A solution of 1M DIBAL (155 ml; 155 mmoles) is added dropwise to a solution of ethyl 4-[[4-(1,1-dimethylethyl)silyl]oxy-1,7-dioxaspiro[5.5]undec-2-yl]-2-methyl-2E-butenoate, (29.0 g; 70.3 mmoles) in methylene chloride (350 ml) with stirring under nitrogen at −78°. Upon completion of the addition, the reaction mixture is allowed to warm to 2° and stirred for two hours. The reaction mixture is cooled to 0° and treated dropwise (slight foaming) with methanol (45 ml). After 15 minutes the reaction mixture is partitioned between methylene chloride (500 ml) and a mixture of 6.67N sulfuric acid (150 ml) and crushed ice (300 g). The mixture is intermittently shaken over a ten minute period. The layers are separated and the aqueous phase extracted with methylene chloride (500 ml). The combined organic phases are dried over anhydrous sodium sulfate, filtered through celite, and concentrated in vacuo to give an oil. Chromatography (15-40% ethyl acetate/hexane) yields the title compound, 4-[[4-(1,1-dimethylethyl)silyl]oxy-1,7-dioxaspiro[5.5]undec-2-yl]-2-methyl-2E-butenol; (21.8 g; 83.8%) as an oil.

Anal.: Calc'd for C$_{20}$H$_{38}$O$_4$Si: C, 64.82; H, 10.34. Found: C, 64.65; H, 10.30.

PMR (CDCl$_3$): 0.15, 0.97, 1.64, 1.78, 2.34, 3.61, 4.10, 5.59 ppm.

EXAMPLE 10

Preparation of 4-[[4-(1,1-dimethylethyl)silyl]oxy-1,7-dioxaspiro[5.5]undec-2-yl]-2-methyl-2E-butanealdehyde To a solution of ethyl 4-[[4-(1,1-dimethylethyl)silyl]oxy-1,7-dioxaspiro[5.5]undec-2-yl]-2-methyl-2E-butenoate, (10.0 g; 27.0 mmoles) in methylene chloride (160 ml) is added finely powdered pyridinium chlorochromate (PCC; 8.7 g; 40.5 mmoles) in a single portion with stirring under nitrogen at 25°. After twenty minutes the reaction mixture is diluted with ether (800 ml) and filtered through celite. The chromium salt residue is washed several times with ether, the washes filtered through celite, and the combined filtrates reduced in volume to 100 ml, filtered through silica gel and concentrated in vacuo to an oil. Chromatography (7.5% ethyl acetate/hexane yields the title compound, 4-[[4-(1,1-dimethylethyl)silyl]oxy-1,7-dioxaspiro[5.5]undec-2-yl]-2-methyl-2E-butanealdehyde; (5.42 g; 54.5%0 as an oil.

PMR (CDCl$_3$): 0.16, 0.97, 1.77, 2.63, 3.59, 4.15, 6.70, 9.51 ppm.

EXAMPLE 11

Preparation of 2,6-dimethylphenyl 2,4-dimethyl-6-[[4-(1,1-dimethylethyl)dimethylsilyl]oxy-1,7-dioxaspiro[5.5]undec-2-yl]-3-hydroxy-4E-hexenoate To a solution of diisopropylamine (1.0 ml; 7/08 mmoles) in THF (15 ml) at 0° under nitrogen is added dropwise a solution of 1.6M n-butyl lithium in hexane (4.4 ml; 7.08 mmoles). After fifteen minutes the reaction mixture is cooled to −78° and a solution of 1,6-dimethylphenyl propionate (1.26 g; 7.08 mmoles) in THF (10 ml) added dropwise. After 60 minutes, a solution of 4-[[4-(1,1-dimethylethyl)silyl]oxy-1,7-dioxaspiro[5.5]undec-2-yl]-2-methyl-2E-butanealdehyde, (2.61 g; 7.08 mmoles) in THF (10 ml) is added dropwise. After ten minutes the reaction is quenched by the rapid addition of saturated ammonium chloride solution (2.5 ml) then allowed to warm to 0°. The mixture is diluted with water (100 ml) and extracted with ether (2×100 ml). The organic phases are combined, washed with 1% hydrochloric acid and then dried over anhydrous magnesium sulfate. Concentration in vacuo gives an oil which is chromatographed (10% ethyl acetate/hexane) to yield the title compound, 2,6-dimethylphenyl 2,4-dimethyl-6-[[4-(1,1-dimethylethyl)dimethylsilyl]oxy-1,7-dioxaspiro[5.5]undec-2-yl]-3-hydroxy-4E-hexenoate; (1.82 g; 47%) as a semi-solid.

Anal.: Calc'd for C$_{31}$H$_{50}$O$_5$Si: C, 68.09; H, 9.22. Found: C, 67.75; H, 9.26

PMR (CDCl$_3$): 0.16, 0.98, 1.33, 1.73, 2.28, 2.38, 3.05, 3.63, 4.12, 4.37, 5.70, 7.12 ppm.

EXAMPLE 12

Preparation of 2,6-dimethylphenyl 2,4-dimethyl-6-[[(4-(1,1-dimethyl)dimethylsilyl]oxy-1,7-dioxaspiro[5.5]-undec-2-yl]-3-(methoxymethyl)oxy-4E-hexenoate To a solution of 2,6-dimethylphenyl 2,4-dimethyl-6-[[4-(1,1-dimethylethyl)dimethylsilyl]oxy-1,7-dioxaspiro[5.5]undec-2-yl]-3-hydroxy-4E-hexenoate, (1.66 g; 3.04 mmoles) and diisopropylethylamine (1.16 ml; 6.68 mmoles) in methylene chloride (5 ml) at 0° is added chloromethylmethyl ether (0.46 ml; 6.08 mmoles). The ice bath is removed and the reaction mixture allowed to stir at ambient temperature under nitrogen for 30 hours. The reaction mixture is diluted with water (10 ml) and extracted with ether (2×25 ml). The organic phases are combined, washed with water, saturated sodium chloride solution, then dried over anhydrous magnesium sulfate. Concentration in vacuo gives an oil which is chromatographed (10% ethyl acetate/hexane) to yield the title compound, 2,6-dimethylphenyl 2,4-dimethyl-6-[[(+(1,1-dimethylethyl)dimethylsilyl]oxy-1,7-dioxaspiro[5.5]-undec-2-yl]-3-(methoxymethyl)oxy-4E-hexanoate; (1.49 g; 82.8%) as an oil. The pmr spectrum shows $H_{13}$ as a doublet, J=10.5 Hz, centered at 4.40 ppm indicating anti-isomers. The methylene of the methoxymethyl group appears as a pair of AB quartets. The higher field absorbing proton isomers overlap and display a broad doublet at 4.55 ppm while the lower field protons appear as a quartet centered at 4.73 ppm. Based on the relative peak heights of this quartet the ratio of α and β anti-isomers is 55:45.

Anal.: Calc'd for $C_{33}H_{54}O_7Si$: C, 67.08; H, 9.21. Found: C, 67.19, H, 9.64.

PMR (CDCl$_3$): 0.17, 0.98, 1.27, 1.74, 1.82, 2.30, 2.41, 3.11, 3.37, 3.64, 4.07, 4.33, 4.62, 5.74, 7.13 ppm.

EXAMPLE 13

Preparation of 2,4-dimethyl-6-[[(4-(1,1-dimethylethyl)dimethylsilyl]oxy-1,7-dioxaspiro[5.5]-undec-2-yl]-3-(methoxymethyl)oxy-4E-hexen-1-ol, Compound No. 13.

To a solution of 2,6-dimethylphenyl 2,4-dimethyl-6-[[(4-(1,1-dimethylethyl)dimethylsilyl]oxy-1,7-dioxaspiro[5.5]-undec-2-yl]-3-(methoxymethyl)oxy-4E-hexenoate, (3.30 g; 5.58 mmoles) in methylene chloride (100 ml) at −78° under nitrogen is added dropwise a 1N solution of DIBAL in methylene chloride (13.4 ml; 13.4 mmoles). After 30 minutes the reaction mixture is treated dropwise with methanol (5.0 ml) and then allowed to warm to 0°. The mixture is partitioned between methylene chloride (250 ml) and ice cold 2N sulfuric acid (150 ml) and intermittently shaken over a ten minute period. The organic phase is dried over anhydrous magnesium sulfate, concentrated in vacuo, and chromatographed (20% ethyl acetate/hexane) to give the title compound, 2,4-dimethyl-6-[[(4-(1,1-dimethylethyl)dimethylsilyl]oxy-1,7-dioxaspiro[5.5]-undec-2-yl]-3-(methoxymethyl)oxy-4E-hexen-1-ol.

Anal.: Calc'd for $C_{25}H_{48}O_6Si$: C, 63.52; H, 10.23. Found: C, 63.31; H, 10.15.

PMR (CDCl$_3$): 0.15, 0.76, 0.96, 1.62, 1.67, 2.36, 3.47, 3.72, 3.88, 4.16, 4.60, 5.56 ppm.

EXAMPLE 14

Preparation of 2,4-dimethyl-6-[[(4-(1,1-dimethylethyl)dimethylsilyl]oxy-1,7-dioxaspiro[5.5]-undec-2-yl]-3-(methoxymethyl)oxy-4E-hexenaldehyde, Compound No. 14

To a solution of Preparation of 2,4-dimethyl-6-[[(4-(1,1-dimethylethyl)dimethylsilyl]oxy-1,7-dioxaspiro[5.5]-undec-2-yl]-3-(methoxymethyl)oxy-4E-hexen-1-ol, (404 mg; 0.855 mmoles) in methylene chloride (5 ml) is added finely powdered pyridinium chlorochromate (550 mg; 2.56 mmoles) in a single portion with stirring under nitrogen at 25°. After four hours the reaction mixture is diluted with ether (20 ml), stirred five minutes and filtered through silica gel. The filtrate is concentrated in vacuo to an oil which is chromatographed (10% ethyl acetate/hexane) to yield the title compound, 2,4-dimethyl-6-[[(4-(1,1-dimethylethyl)-dimethylsilyl]oxy-1,7-dioxaspiro[[5.5]-undec-2-yl]-3-(methoxymethyl)oxy-4E-hexenaldehyde; (317 mg; 79%) as an oil.

Anal.: Calc'd for $C_{25}H_{46}O_6Si$: C, 63.79; H, 9.85. Found: C, 63.93; H, 9.77

NMR (CDCl$_3$): 0.15, 0.98, 1.06, 1.64, 1.71, 2.40, 3.43, 3.64, 4.01, 4.23, 4.63, 9.96 ppm.

EXAMPLE 15

Preparation of 3,5-dimethyl-1-[[(4-(1,1-dimethylethyl)dimethylsilyl]oxy-1,7-dioxaspiro[5.5]-undec-2-yl]-4-(methoxymethyl)oxyocta-2E,7-diene-6-ol To a solution of 1M vinylmagnesium bromide in ether (3.0 ml; 3.0 mmoles) at 0° under nitrogen is added THF (2.5 ml) followed by dropwise addition of a solution of aldehyde 3; (1.00 g; 2.12 mmoles) in ether (20 ml). Upon completion of addition the ice bath is removed and the reaction mixture stirred at ambient temperature for five hours. The reaction mixture is diluted with ether (125 ml), washed in turn with saturated ammonium chloride solution and saturated sodium chloride solution and the organic phase dried over anhydrous magnesium sulfate. Concentration in vacuo gives an oil. Chromatography (15% ethyl acetate/hexane) affords 16 (611 mg; 57.6%) as an oil.

PMR (CDCl$_3$): 0.15, 0.83, 0.98, 1.69, 2.38, 3.08, 3.50, 3.64, 4.04, 4.57, 4.74, 5.24, 5.36, 5.50, 5.64, 5.70, 5.97, and 6.18.

The spiroketals of Formula XIX can be used as the pure compounds or as mixtures of pure compounds but for practical reasons the compounds are preferably formulated as anthelmintic compositions and administered as a single or multiple dose, alone or in combination with other anthelmintics (e.g. avermectins, benzimidazoles, levamisole, praziquantel, etc.). For example, aqueous or oil suspensions can be administered orally, or the compounds can be formulated with a solid carrier for feeding. Furthermore, an oil suspension can be converted into an aqueous emulsion by mixing with water and injecting the emulsion intramuscularly, subcutaneously or into the peritoneal cavity.

Pure compounds, mixtures of the active compounds, or combinations thereof with a solid carrier can be administered in the animal's food, or administered in the form of tablets, pills, boluses, wafers, pastes, and other conventional unit dosage forms, as well as sustained release dosage forms which deliver the active compound over an extended period of days, weeks or months. All of these various forms of the active compounds of this invention can be prepared using physiologically acceptable carriers and known methods of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal feed to about 90 or 95 percent of more in a pill or capsule. In the latter form, one might use no more carrier than sufficient to bind the particles of active compound.

In general, the compounds can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active ingredient. A prepared hog-feed containing about 0.2 percent of the active compound will provide a dosage of about 100 mg per kg body weight for each 100 lb pig in its daily ration.

A solid diluent carrier need not be homogeneous entity, but mixtures of different diluent carriers can include small proportions of adjuvants such as water; alcohols; protein solutions and suspensions like skimmed milk; edible oils; solutions, e.g., syrups; and organic adjuvants such as propylene glycols, sorbitol, glycerol, diethyl carbonate, and the like.

The solid carrier formulations of the inventions are conveniently prepared in unit dosage forms, to facilitate administration to animals. Accordingly, several large boluses (about 20 g weight) amounting to about 54 g of active compound would be required for a single dosage to a 900 lb horse at a dosage rate of 50 mg/kg of body weight. Similarly, a 60 lb lamb at a dosage rate of 100 mg/kg of body weight would require a pill, capsule, or bolus containing about 2.7 g of active compound. A small dog, on the other hand, weighing about 20 lbs. would require a total dosage of about 225 mg at a dosage rate of 25 mg/kg of body weight. The solid, unit dosage forms can be conveniently prepared in various sizes and concentrations of active ingredient, to accommodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as cationic, anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose, methylcellulose, sodium polyvinylpyrrolidone, and the like. The proportion of the active compound in the aqueous suspensions of the invention can vary from about 1 percent to about 20 percent or more.

Oil solutions are prepared by mixing the active compound and an oil, e.g. an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. One can also administer a sustained release dosage system (protracted delivery formulation) so as to provide therapeutic and/or prophylactic dosage amounts over an extended period. Unit dosage forms in accordance with this invention can have anywhere from less than 1 mg to 500 g of active compound per unit.

Although the anthelmintic agents of this invention will find their primary use in the treatment and/or prevention of helminth parasitisms in domesticated animals such as sheep, cattle, horses, dogs, swine, goats and poultry, they are also effective in treatment that occurs in other warm blooded animals including man. The optimum amount to be employed for best results will, of course, depend upon the particular spiroketal compound employed, species of animal to be treated, the regimen treatment and the type and severity of helminth infection. Compounds of Formula XIX can be administered by the oral or parenteral route of administration at a dose of about 0.2 to 200 mg/kg of animal bodyweight (such total dose being given at one time, in a protracted manner or in divided doses over a short period of time such as 1–4 days). The technique for administering these materials to animals are known to those skilled in the veterinary and medical fields.

2,4-Dimethyl-6-[[4-(1,1-dimethylethyl)dimethylsilyl]oxy-1,7-dioxaspiro[5.5]undec2-yl]-3-(methoxymethyl)oxy-4E-hexen-1-ol, Compound No. 13, and 2,4-dimethyl-6-[[(-(1,1-dimethyletheyl)dimethylsilyl]oxy-1,7-dioxaspiro[5.5]-undec-2-yl]-3-(methoxymethyl)oxy-4E-hexenaldehyde, Compound No. 14, have demonstrated a minimum effective concentration of 2 ppm and 20 ppm, respectively, against the free living nematode *Caenorhabditis elegans* in accordance with Procedure 1.

Compounds No. 13 and 14 have also been tested at 600 mg/Kg against *S. obvelata* and *N. dubius* in mice in accordance with Procedure No. 2 and demonstrated activity as set forth in Table I.

TABLE I

|  | % Clearance | |
|---|---|---|
|  | S. obvelata | N. dubius |
| Compound #14 | 40% | 80% |
| Compound #13 | 20–100% | 25–40% |

In a trial in sheep, in accordance with Procedure 3, at oral doses of 2 and 20 mg/kg, no activity against *H. contortus* was observed with Compound No. 13. However, at higher dosages and/or against other worms anthelmintic activity is anticipated.

In a trial in sheep, in accordance with Procedure 3, at oral doses of 2 and 14.4 mg/kg, 24% and 30% clearance, respectively, against *H. contortus* was observed with Compound No. 14.

DEFINITIONS

The definitions and explanations below are for the terms as used throughout the entire patent application including both the specification and claims.

All temperatures are in degrees Celsius.

TLC refers to thin-layer chromatography.

Brine refers to an aqueous saturated sodium chloride solution.

When solvent pairs are used, the ratio of solvents used are volume/volume (v/v).

DIBAL refers to diisobutylaluminum hydride.

DMF refers to dimethylformamide.

THF refers to tetrahydrofuran.

PMR refers to proton magnetic resonance spectroscopy, chemical shifts are reported in ppm ($\delta$) downfield from TMS.

TMS refers to tetramethylsilane.

Procedure 1

Materials and Methods: Media Preparation—Nematode Growth Agar (NGA) Plates—3 g NaCl, 2.5 g Bactopeptone, and 17 g Bactoagar are mixed in 975 ml of distilled water plus 1 ml of a 5 mg/ml solution of cholesterol in ethanol. The resulting mixture is autoclaved at 120° for 20 minutes, and then 1 ml $CaCl_2$, 1 ml 1M $MgSO_4$, and 25 ml 1M $KH_2PO_4$ (pH 6.0), each sterile filtered, are added to the mixture. Immediately thereafter 15 ml quantities are plated aseptically into 100×20 mm plastic petri dishes (tissue culture grade). NGA plates are stored at 4° C. until needed.

Nematode Washing Buffer (M9 buffer)—6 g $Na_2HPO_4$, 5 g NaCl, and 0.25 g $MgSO_4.7H_2O$ are mixed in 1 liter of distilled water. Suitable volumes (50, 90, and 450 ml) are dispensed into Erlenmeyer flasks and autoclaved for 20 minutes at 120°. M9 buffer is stored at 4° C. until needed.

*Escherichia coli* Streak-Plates—8 g NaCl, 10 g Bactotryptone, 5 g yeast extracts, 15 g agar, and 5 mg thymidine are added to 500 ml of distilled water and mixed well, after which the volume is brought to 1 liter with distilled water. The mixture is autoclaved at 120° C. for 20 minutes, and then 15 ml quantities are plated aseptically into 100×20 mm plastic petri dishes (tissue culture grade). These plates are stored at 4° C. until needed.

*Escherichia coli* broth—The same ingredients are used as for *E. coli* streak-plates except the agar is omitted and 10 mg cysteine is added. Aliquots of 10 ml are dispensed into disposable scintillation vials and the lightly capped vials are autoclaved for 20 minutes at 120° C. These are stored at 4° C. until needed.

Maintenance of *C. elegans*—A culture of *C. elegans* is maintained at 20° C. on NGA plates seeded with an uracil-requiring mutant of *Escherichia coli*. A few nematodes (any stage) are aseptically transferred to fresh NGA plates weekly; separate NGA plates from each transfer are used the following week for screening trials and for subsequent transfers. One week prior to *C. elegans* transfers, NGA plates are seeded aseptically when 1 ml of broth containing a 4-day-old growth of *E. coli* which is spread evenly across the plate to produce an *E. coli* lawn. The *E. coli* mutant required for maintenance of *C. elegans* also is transferred aseptically to fresh streak-plates weekly; separate streak-plates are used to inoculate broth tubes (for use in screening trials or to seed NGA plates) at 3 days posttransfer or to inoculate fresh streak-plates, one week after transfer. *Escherichia coli* streak-plates, *E. coli* broth tubes, and NGA plates seeded with *E. coli* are maintained at room temperature (20°–23° C.)

Screening Trials—The test medium is prepared on the day a screening trial is to be initiated and consists of 9 parts M9 buffer and 1 part *E. coli* broth containing well grown (3-4 days) *E. coli*. In addition, ampicillin (50 µg/ml) and nystatin (100 U/ml) are added to the test medium which is then allowed to stand at room temperature for 2 hours. During the 2-hour waiting period all test substances (10 and 30 mg quantities) are dissolved in 1 ml of DMSO. Following the waiting period, the test medium is dispensed, 2 ml per well, into Sterilin Repli Dishes (square, 25-well covered dishes). Each well then receives 10 µl of a test substance (23 wells per dish) or 10 µl of a standard (1 well per dish) or is used as a nontreated control (1 well per dish). This provides "in well" effective concentrations of 50 and 150 ppm for each test substance. Once all wells have been charged, 20-25 C. elegans (all stages of development) are added to each well in a drop of M9 buffer. The worm suspension is prepared immediately prior to use by rinsing a 1-week-old *C. elegans* culture into an Erlenmeyer flask containing M9 buffer; this suspension is then diluted with M9 buffer until the desired 20-25 worms per drop concentration is reached. Following the addition of *C. elegans* to each well, the plates are incubated for 1 week at 20° C. in the dark.

Readings of Screening Trial Results—Readings are made with a dissecting microscope on each well after both 3 and 7 days of incubation. The nontreated and standard wells are read first to determine that all is in order for each dish. Nontreated wells should show a significant increase in worm numbers (up to 50-fold,) while a standard treatment should contain no or very few live worms. Test substances are scored based primarily on worm numbers, although appearance, movement, and developmental stages present also can influence scoring.

The results are reported as minimum effective concentration (mec) as defined by K. G. Simpkin and G. C. Coles, J. Chem. Tech. Biotechnol., 31, p66, 1981.

Procedure 2

Mice are infected with *S. obvelata* and *N. dubius*. Fresh caecal contents containing *S. obvelata* are mixed with corn meal and fed to mice which had been starved for 24 hours. The mice are then placed into community cages with other mice known to have patent infections of *S. obvelata* and monitored until high levels of infection are observed at necropsy in randomly selected indicator animals. Each mouse is then given ~100 infective larvae of *N. dubius* per os. Two weeks later mice from each community cage are sacrificed and examined for both helminth species. Following sampling, the remaining animals are randomly allotted to treated groups of five mice/group. Throughout the experiments mice receive food and water ad lib.

Test compounds are evaluated orally in five mouse groups at 600 mg/kg. Oral treatments are administered with a 1 cc tuberculin syringe fitted with a cannula. Each mouse receives ¼ of the test dose/day on four consecutive days in 0.1 ml of vehicle (40% glycerol formal, 5% polyvinylpyrrolidone C-15 in propylene glycol). In each separate experiment ten mice are used as non-treated controls.

All mice in each trial are sacrificed three days after the last treatment and examined for *N. dubius* and *S. obvelata*. The clearance rate is calculated according to the following formula:

$$\text{Clearance rate} = \frac{\text{number of mice cleared}}{\text{number of mice treated}} \times 100$$

Procedure 3

In individual experiments all sheep are treated identically, however non-critical variations occur between experiments. All of the sheep used in this procedure are treated twice with levamisole hydrochloride orally at 8 mg/kg or once each with ivermectin parenterally at 200 µg/kg and levamisole hydrochloride orally at 8 mg/kg. The second treatment in each case is administered 4–7 days after the first treatment. Two weeks after the second treatment all sheep are inoculated per os with ~3,500 to ~7,500 infective larvae of *H. contortus*. Rectal fecal samples are taken from each sheep 26–41 days post-inoculation (PI), and these samples are examined for eggs of *H. contortus* using the McMaster counting chamber technique. All sheep harboring good infections of *H. contortus* are randomly allocated to a treatment group; those which do not exhibit suitable infections are dropped from the study. One to three days later on days 27–42 PI each sheep remaining in the study (excluding the non-treated controls) is treated with a test compound (orally or parenterally at 100 mg/kg unless indicated otherwise) or a standard (levamisole hydrochloride orally at 8 mg/kg) or is used as an untreated control. All sheep received food and water ad lib. throughout the experiment.

Prior to administration, all solid compounds are finely ground using a mortar and pestle. Oral compounds are suspended in 20–30 ml of sterile vehicle #98 (each ml contains: carboxymethylcellulose—10 mg, polysorbate 80—4 mg, propylparaben—0.42 mg) using a sonicator and administered along with a tap water wash via a stomach tube. The parenteral compounds are similarly suspended in 20–30 ml of the sterile vehicle and given by intraperitoneal injection using a 13 gauge, 2 inch needle and a 50 ml syringe. All test compounds are given to a single sheep/route of administration. Two or more sheep are treated with levamisole hydrochloride and five are used as non-treated controls. All animals are monitored for signs of toxicity following treatment.

The sheep are sacrificed 7–12 days after treatment (days 35–49 PI), and the abomasum is ligated and removed from each sheep. Each abomasum is longitudinally sectioned and rinsed into an 80 mesh sieve. Sieve contents are collected in individual containers and fixed in formol-alcohol. Later each sample is transferred to a 1000 or 2000 ml beaker and the volume brought to 400–1000 ml with tap water. The total number of worms in a 40–100 aliquot (10%) is determined. When no worms are found in the 10% aliquot, the entire sample is examined. Total worm number/sheep and percentage clearance for each treatment are calculated. Percentage clearance for a particular test compound in a given trial is determined according to the following formula:

Percentage Clearance (Test Compound) = [(Mean number of worms recovered from non-treated control sheep − Number of worms recovered from treated sheep)/Mean number of worms recovered from non-treated control sheep] × 100.

Sheep which die within 24 hr following treatment are not examined for worms, while any that die between 24 hr post-treatment and necropsy are examined in an identical manner as that described above.

FORMULAE

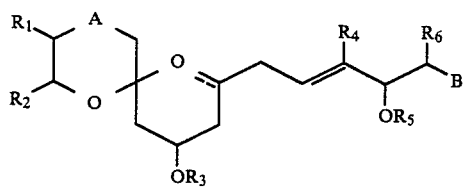

XIX

-continued
FORMULAE

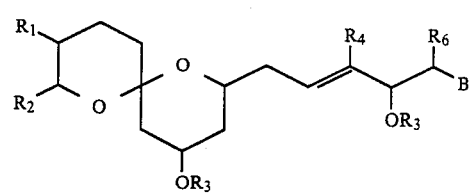

XIXa

SCHEME A

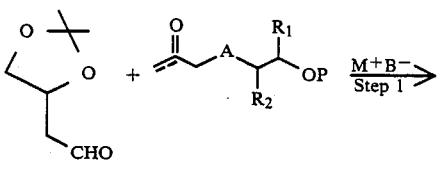

I  II

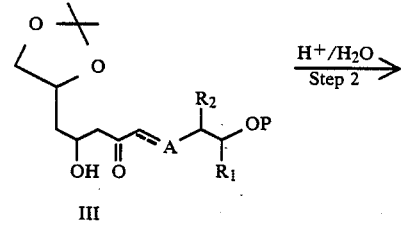

III

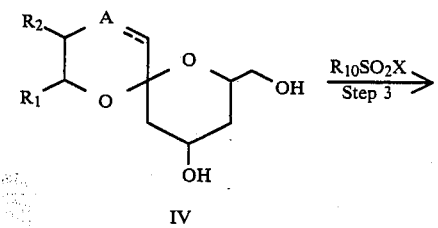

IV

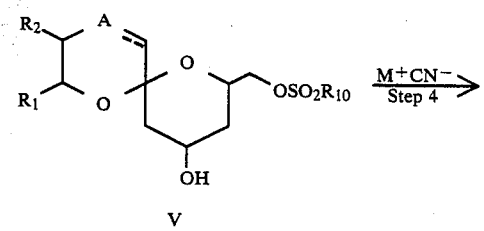

V

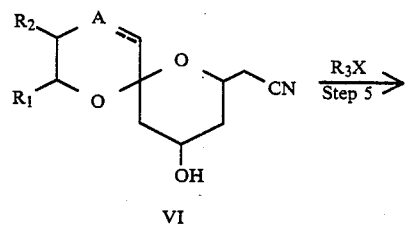

VI

-continued
SCHEME A
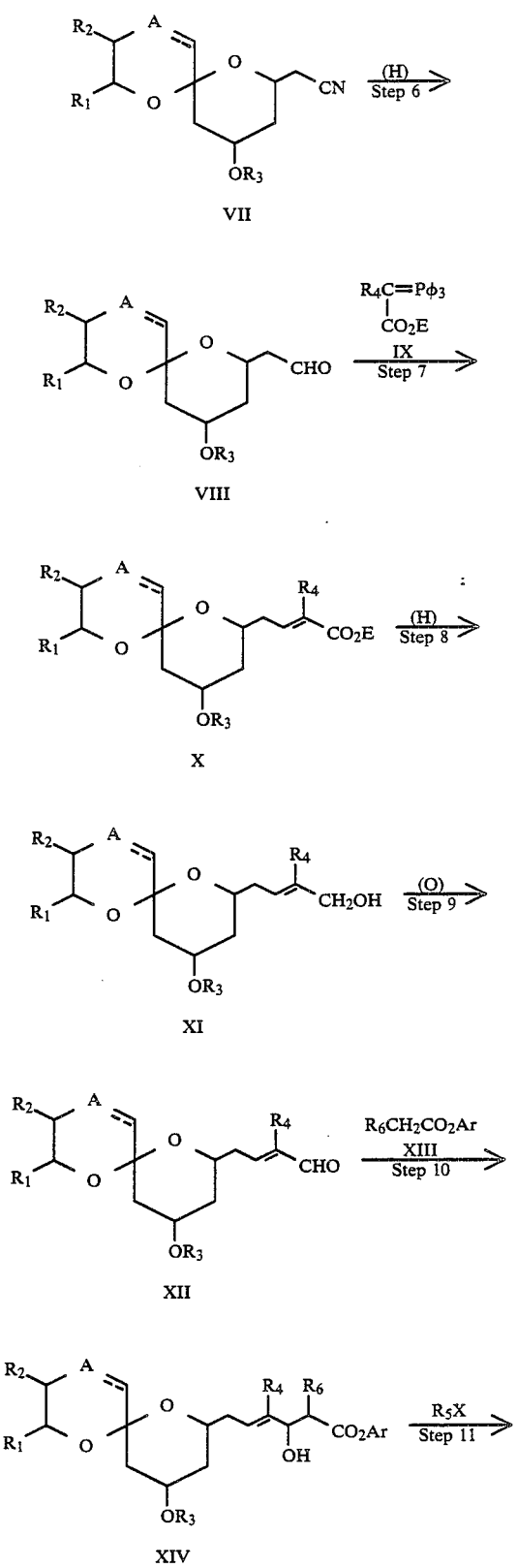
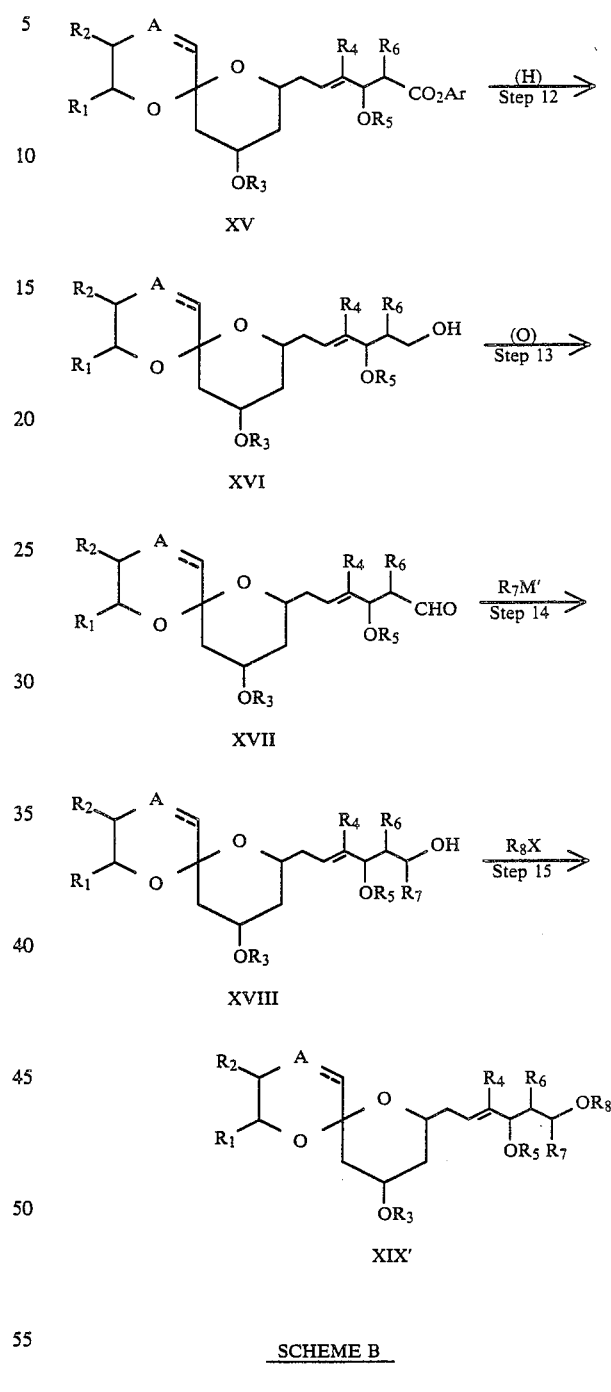
SCHEME B
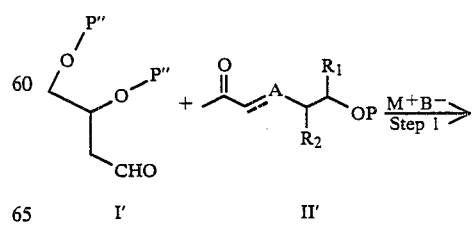

-continued
SCHEME B
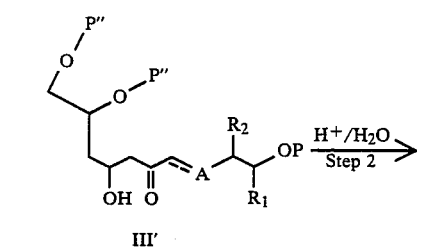
III'
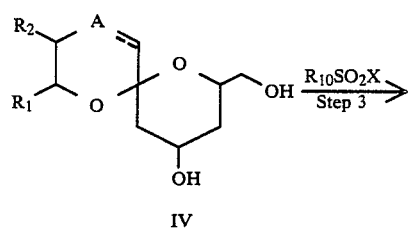
IV
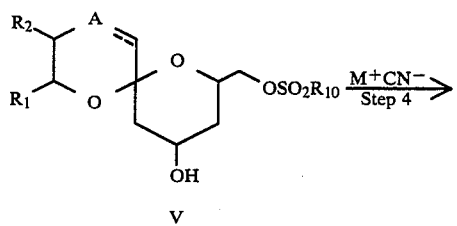
V
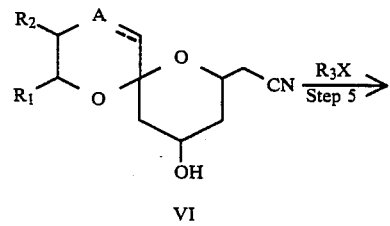
VI
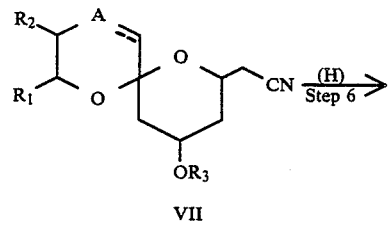
VII
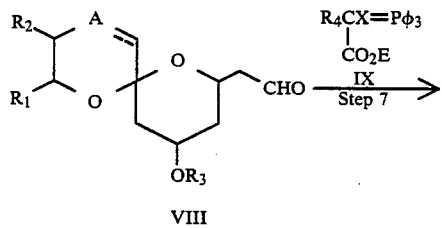
VIII
-continued
SCHEME B
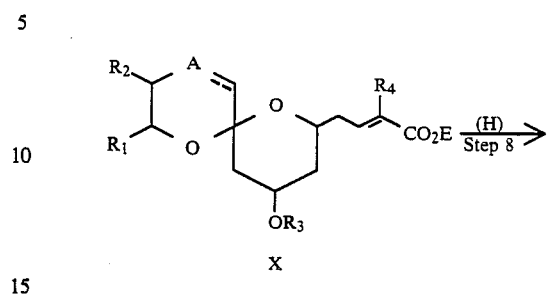
X
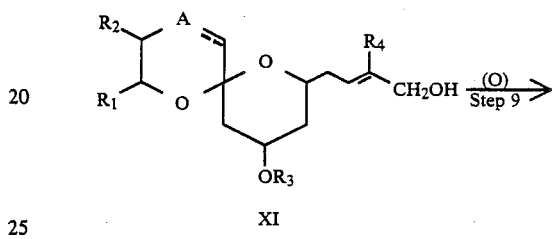
XI
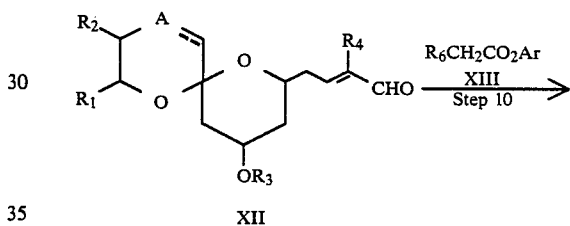
XII
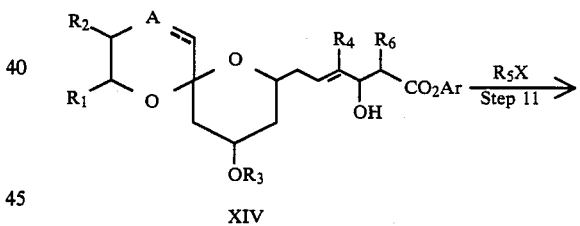
XIV
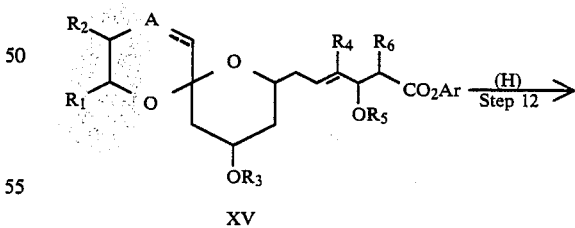
XV
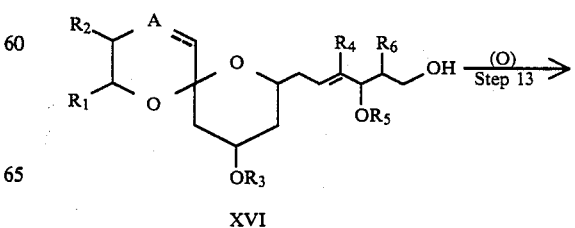
XVI -continued
SCHEME B

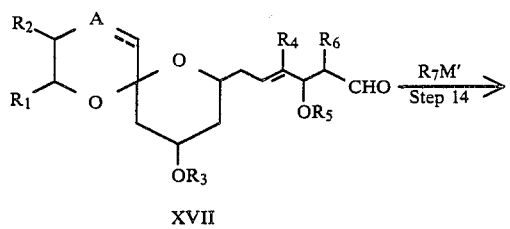

XVII

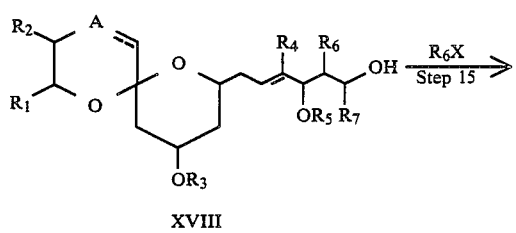

XVIII

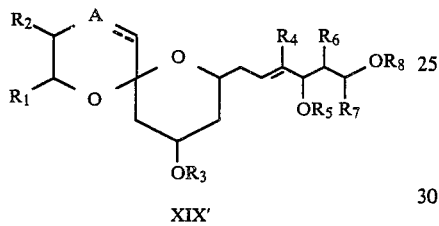

XIX'

I claim:
1. A compound of the formula:

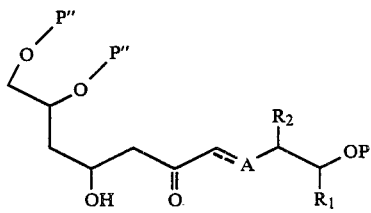

III' wherein P is $C_1$-$C_5$ alkyl; benzoyl optionally substituted with one, 2 or 3 $C_1$-$C_4$ alkyl, $C_1$-$C_3$ alkoxy, halo, $C_1$-$C_3$ alkylthio, trifluoromethyl, nitro; phenyl($C_1$-$C_3$)alkyl optionally substituted with one, 2 or 3 $C_1$-$C_4$ alkyl, $C_1$-$C_4$ alkoxy, halo, nitro or trifluoromethyl; $C_2$-$C_6$ alkoxyalkyl; $C_2$-$C_6$ alkylthioalkyl; $C_1$-$C_6$ alkanoyl; 2-tetrahydropyranyl; $C_1$-$C_4$ alkyl diphenyl silyl; di($C_1$-$C_4$ alkyl) phenyl silyl; or tri($C_1$-$C_4$)alkyl silyl;

wherein P'', being the same or different, are $C_1$-$C_5$ alkyl; benzoyl optionally substituted with one, 2 or 3 $C_1$-$C_4$ alkyl, $C_1$-$C_3$ alkoxy, halo, $C_1$-$C_3$ alkylthio, trifluoromethyl, nitro; phenyl($C_1$-$C_3$)alkyl optionally substituted with one, 2 or 3 $C_1$-$C_4$ alkyl, $C_1$-$C_4$ alkoxy, halo, nitro or trifluoromethyl; $C_2$-$C_6$ alkoxyalkyl; $C_2$-$C_6$ alkylthioalkyl; $C_1$-$C_6$ alkanoyl; 2-tetrahydropyranyl; $C_1$-$C_4$ alkyl diphenyl silyl; di($C_1$-$C_4$ alkyl) phenyl silyl; or tri($C_1$-$C_4$)alkyl silyl; or optionally taken together to form a 1,3-dioxolane ring optionally substituted with one or two $C_1$-$C_5$ alkyl;

wherein A is —CH, —$CH_2$ or —CHOP';

wherein P' is $C_1$-$C_5$ alkyl; benzoyl optionally substituted with one, 2 or 3 $C_1$-$C_4$ alkyl, $C_1$-$C_3$ alkoxy, halo, $C_1$-$C_3$ alkylthio, trifluoromethyl, nitro; phenyl($C_1$-$C_3$)alkyl optionally substituted with one, 2 or 3 $C_1$-$C_4$ alkyl, $C_1$-$C_4$ alkoxy, halo, nitro or trifluoromethyl; $C_2$-$C_6$ alkoxyalkyl; $C_2$-$C_6$ alkylthioalkyl; $C_1$-$C_6$ alkanoyl; 2-tetrahydropyranyl; $C_1$-$C_4$ alkyl diphenyl silyl; di($C_1$-$C_4$ alkyl) phenyl silyl; or tri($C_1$-$C_4$)alkyl silyl;

wherein is a single bond when A is —$CH_2$ or —CHOP' and a double bond when A is —CH; and wherein $R_1$ and $R_2$, being the same or different, are hydrogen or $C_1$-$C_5$ alkyl.

2. A compound according to claim 1 wherein P'' are taken together to form the 2,2-dimethyl-1,3-dioxolane ring system.

3. The compound according to claim 1 wherein A is —$CH_2$, $R_1$ and $R_2$ are hydrogen, and P it t-butyldimethylsilyl so that the compound is 8-t-butyldimethylsilyloxy-1-(2,2-dimethyl-1,3-dixolan-4-yl)-2-hydroxyoctan-4-one.

* * * * *

UNITED STATES PATENT OFFICE
CERTIFICATE OF CORRECTION

Patent No. 4,812,582　　　　　　　　　　　Dated 14 March 1989

Inventor(s) S.J. Nelson

It is certified that error appears in the above-identified patent and that said Letters Patent is hereby corrected as shown below:

Column 24, line 32 which reads "wherein　is a" should read: --wherein .... is a--.
Column 24, line 40 which reads "P it" should read: --P is--.

Signed and Sealed this

Twenty-sixth Day of December, 1989

Attest:

JEFFREY M. SAMUELS

Attesting Officer　　　Acting Commissioner of Patents and Trademarks